United States Patent [19]

Brennan et al.

[11] Patent Number: 4,931,557

[45] Date of Patent: Jun. 5, 1990

[54] METHOD OF RESOLVING CIS 3-AMINO-4-(2-FURYL)VINYL)-1-METHOX-YCARBONYLMETHYL-AZETIDIN-2-ONE AND DI-P-TOLUOYL-TARTARIC ACID SALTS THEREOF

[75] Inventors: John Brennan; Thomas M. Eckrich, both of Indianapolis, Ind.

[73] Assignee: Eli Lilly and Company, Indianapolis, Ind.

[21] Appl. No.: 258,918

[22] Filed: Oct. 17, 1988

[51] Int. Cl.$^5$ .................... C07B 57/00; C07D 407/06
[52] U.S. Cl. .................................................... 540/364
[58] Field of Search ........................................ 540/364

[56] References Cited

U.S. PATENT DOCUMENTS

| 4,003,913 | 1/1977 | Demerson | 548/508 |
| 4,072,698 | 2/1978 | Hylton et al. | 548/505 |
| 4,248,880 | 2/1981 | Krasso | 548/326 |
| 4,665,171 | 5/1987 | Evans et al. | 540/364 |

OTHER PUBLICATIONS

Blaschke, Chem. Abs. 107, 58591u (1987).
Howe, Chem. Abs. 83, 57233 (1975).
Nemy, Chem. Abs. 87, 193907d (1977).
Zoelss, Chem. Abs. 104, 206931d (1985).
Yost, Chem. Abs. 92, 94098n (1979).
Kametani, Chem. Abs. 85, 108849c (1976).
Hatanaka et al., "A Simple Synthesis of (±)-1-Carbacephem Derivatives", *Tetrahedron Letters*, vol. 24, No. 44, pp. 4837–4838 (1983).

*Primary Examiner*—Mark L. Berch
*Attorney, Agent, or Firm*—Bernard J. Graves, Jr.; Leroy Whitaker

[57] ABSTRACT

Cis $\alpha\alpha$, $\beta\beta$-3-amino-4-[2-(2-furyl)vinyl-1-yl]-1-methoxycarbonylmethyl-azetidin-2-one is resolved via optically active di-p-toluoyl tartaric acid.

2 Claims, No Drawings

METHOD OF RESOLVING CIS 3-AMINO-4-(2-FURYL)VINYL)-1-METHOXYCAR-BONYLMETHYL-AZETIDIN-2-ONE AND DI-P-TOLUOYL-TARTARIC ACID SALTS THEREOF

BACKGROUND OF THE INVENTION

An important clinical trial candidate, (6R, 7S) 7-(R)-phenylglycylinamido-3-chloro-1-azabicyclo[4.2.0]oct-2-en-8-on-2-carboxylic acid (loracarbef) may be synthesized by various routes. One of the more noteworthy total syntheses of loracarbef is that made possible by Evans and Sjogren, U.S. Pat. No. 4,665,171. The Evans and Sjogren methodology provides a chiral 2+2 (ketene plus imine) cycloaddition, and accordingly, entry to a wide variety of chiral, cis β-lactams. However, the Evans and Sjogren methodology provides for the utilization of a chiral auxiliary of the formula

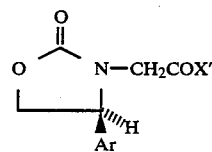

in the 2+2 cycloaddition with a Schiff's base, wherein X' is chloro, bromo, trifluoroacetoxy, or $-OP(=)X_2$, wherein X is halogen. The above chiral auxiliary is synthesized in seven steps from (L)-phenylglycine. The resulting cycloaddition provides compounds of the formula

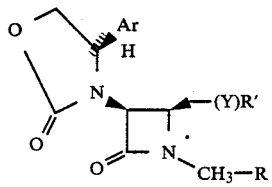

wherein Ar is phenyl, $C_1$-$C_4$ alkylphenyl, halophenyl, $C_1$-$C_4$ alkoxyphenyl, naphthyl, thienyl, furyl, benzothienyl, or benzofuryl; R is phenyl, $C_1$-$C_4$ alkylphenyl, $C_1$-$C_4$ alkoxyphenyl, or halophenyl; Y is $-CH=CH-$, or $-CH_2-CH_2-$; and R' is phenyl, $C_1$-$C_4$ alkylphenyl, $C_1$-$C_4$ alkoxyphenyl, halophenyl, furyl or naphthyl.

The obvious shortcomings of the Evans and Sjogren route are that a very expensive starting material, L-phenylglycine, is used; the chiral auxiliary is synthesized in several steps in linear fashion; and finally, the chiral auxiliary is removed and discarded using $Li/NH_3/t$-$C_4H_9OH$ to provide a free 3-amino-azetidinone.

As an achiral alternative, Hatanaka et al., Tetrahedron Letters Vol. 24, No. 49, pp 4837–4838 (1983), provides a method of preparing a 3-hydroxy(±)-1-carbacephalosporin via a 2+2 cycloaddition much in the same fashion as that of Evans and Sjogren, but without the use of a chiral auxiliary as the ketene source. The Hatanaka methodology provides many of the same intermediates as does the Evans and Sjogren synthesis, albeit in achiral form. The advantage of the achiral synthesis is economy of steps and starting material.

The present invention affords a useful alternative to the challenge of synthesizing 1-carba(1-dethia)cephalsoporins by providing a method for resolution of a key achiral cis-azetidinone intermediate provided by achiral cis-2+2 cycloaddition. In particular, the present invention provides a method for resolution of an achiral intermediate in the total synthesis of 1-carba(1-dethia)cephalsoporins using di-p-toluoyl-tartaric acid.

SUMMARY

Cis 3-amino-4-[2-(2-furyl)vinyl]-1-methoxycarbonylmethyl-azetidin-2-one is resolved by the practice of this invention into its enantiomeric cis α,α and cis β,β components, whereby the desired cis β,β enantiomer is selectively crystallized from solution using di-p-toluoyl-(D)-tartaric acid.

DESCRIPTION OF THE INVENTION

The present invention provides a method of resolving cis α,α/β,β azetidinone represented by the following two enantiomers:

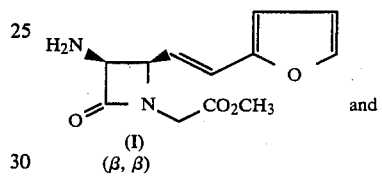

and

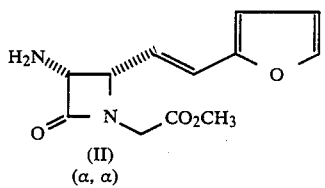

to yield optically pure isomers, each free of the other. This resolution is accomplished by dissolving a racemic mixture of I and II in a polar organic solvent, preferably acetonitrile or 1,2-dichloroethane, and warming the solution to approximately 50° C. Di-p-toluoyl-(D)-tartaric acid is then added and the solution allowed to cool to room temperature gradually overnight, thus forming the diasteromeric di-p-toluoyl-(D)-tartaric acid salt of (I) in excellent yield and outstanding optical purity. The resulting free amino enantiomer (I) is then provided by routine acid/base workup.

One skilled in the art will appreciate that the selective crystallization of one diastereomer from a polar organic solution is also affected by concentration. A relatively low concentration provides a diastereomer of generally higher purity but lower yield, while the utilization of a higher concentration of racemate and resolving agent will normally provide higher yields of solid, many times at the expense of optical purity. Thus, the preferred concentration range for the present invention in tetrahydrofuran or $CH_3CN$ is about 0.25M to about 0.75M, preferably about 0.5M.

The corresponding α,α enantiomer (II) is provided by the same manipulations as above by merely substituting di-p-toluoyl-(L)-tartaric acid as the resolving agent.

As a further aspect of the present invention, in addition to the process for resolving the racemic mixture of I and II above, there is provided the di-p-toluoyl-(D)- tartaric acid salt of (I) and the di-p-toluoyl-(L)-tartaric acid salt of (II).

A number of optically active acids were explored as potential resolving agents along with several different solvent systems. Table 1 below summarizes the results of these experiments (an X designates when a solid was obtained):

TABLE 1

|  | $H_2O$ | EtOH | DMF | 1DMF | 9 EtOH/ DMSO | THF | EtOAC | ACN | Acetone | 1,2 DCE |
|---|---|---|---|---|---|---|---|---|---|---|
| D(−)Mandelic acid | | | | | | | | | | |
| D-10-Camphorsulfonic acid | | | | | | | | | | |
| 1-α-bromocamphorsulfonic acid | | | | | | | | | | |
| $NH^4$ L(+) tartaric acid | | | | | | X | | | | |
| Dibenzoy-1-Tartaric.$H_2O$ acid | | | | | | | | | | |
| D (+) Malic acid | | | | | | | | | | |
| Di-p-toluoyl-1-tartaric.$H_2O$ acid | | | | | | | X | X | | X |
| L(−) N-benzoyl-α-alanine acid | | | | | | | | | | |
| Quinic acid | | | | | | | | | | |
| L-Menthoxy acetic acid | | | | | | | | | | |
| D-Camphoric acid | | | | | | | | | | |
| L-2-pyrrolidone-5-carboxylic acid | | | | | | | | X | | X |
| (−) 3-Pinaecarboxylic acid | | | | | | | | X | | |
| L-Malic acid | | | | | | | | | | |
| Abietic acid | | | | | | | | | | |
| L(+) Aspartic acid | | | | | | | | | | |
| N-acetyl glutamic acid | | | | | | | | | | |

[Legend: EtOH = ethanol; DMF = dimethylformamide; DMSO = dimethyl-sulfoxide; THF = tetrahydrofuran; EtOAc = ethyl acetate; ACN = acetonitrile; 1,2 DCE = 1,2 dichloroethane]

Table 2 below summarizes the results of the analysis of the solids obtained in the experiments represented by Table 2:

TABLE 2

| Resolving Agent | Solvent | Yield | Composition |
|---|---|---|---|
| 1-(+)-Tartaric acid | tetrahydrofuran | 50.5% | Racemic |
| Di-p-toluoyl-(D)-tartaric acid | ethyl acetate | 7.6% | 21% β,β enantiomeric excess (ee) |
| Di-p-toluoyl-(D)-tartaric acid | acetonitrile | 15.0% | 94% ee β,β |
| Di-p-toluoyl-(D)-tartaric acid | 1,2-dichloroethane | 3.0% | 96% ee β,β |
| D-camphoric acid | acetonitrile | 15.3% | No amine |
| D-camphoric acid | 1,2-dichloroethane | 36.0% | No amine |
| Pinane carbox. acid | acetonitrile | 15.0% | No amine |
| Di-p-toluoyl-(L)-tartaric acid | acetonitrile | 11.0% | 95.6% ee α,α |

As it is clear from Tables 1 and 2, efficient resolution of the β,β-isomer (I) may be obtained utilizing di-p-toluoyl-(D)-tartaric acid as the resolving agent and acetonitrile and 1,2-dichloroethane as preferred solvents.

It is also noteworthy that the use of di-p-toluoyl-(L)-tartaric acid as resolving agent provides the α,α-isomer (II) in high enantiomeric excess.

As a further aspect of the present invention, there are provided the novel di-p-toluoyl-(D)tartaric acid salt of cis β,β-3-amino-4-[2-(2-furyl)vinyl]-1-yl-1-methoxycarbonylmethyl-azetidin-2-one and the di-p-toluoyl-(L)-tartaric acid salt of cis α,α-3-amino-4-[2-(2-furyl)vinyl]-1-yl-1-methoxycarbonylmethyl-azetidin-2-one.

The diastereomeric salt formed in the process is separated from the resolution mixture and the free amino azetidinone is recovered from the salt form by conventional methods. For example, the salt is treated in an aqueous medium with a base to form the free amine which can be extracted from the aqueous phase with a water immiscible solvent such as ethyl acetate. The process provides a high degree of separation of the two enantiomeric azetidinones as reflected by the observed enantiomeric excess (ee) of the product. While as a preferred aspect of the invention the β,β isomer (I) is crystallized out as its di-p-toluoyl-(D)-tartaric acid salt, it is appreciated by one skilled in the art that di-p-toluoyl-(L)-tartaric acid may be substituted, thereby selectively crystallizing the α,α isomer (II) away from the racemic mixture. Exhaustive crystallization of the α,α isomer (II) would thus leave mother liquors containing the β,β isomer (I) in high optical purity.

The following examples are set forth to further describe the invention but are in no way meant to be construed as limiting the scope thereof.

EXAMPLE 1

Di-p-toluoyl-(D)-tartaric acid salt of cis β,β-amino-4-[2-(2-furyl)vinyl]-1-methoxycarbonyl-methyl-azetidin-2-one A 1.0 g (4 mMol) sample of cis αα/ββ-4-[2-(2-furyl)vinyl]-1-yl-1-methoxycarbonylmethyl-azetidin-2-one and 1.618 g (4 mMol) of di-p-toluoyl-(D)-tartaric acid were suspended in 8 ml of acetonitrile and heated to 50° C. and allowed to stir overnight, gradually cooling to room temperature. The resulting solid was filtered and washed with acetonitrile to provide 370 mg of the title compound.

The mother liquors were diluted with 8 ml of acetonitrile and the mixture refrigerated for 5 hr. The resulting solid was filtered and washed with acetonitrile to provide an additional 262 mg of the title compound.

Yield (both crops)=632 mg (48.3% of one enantiomer); ee=98.95%. The 3,5-dinitrobenzamide of the title compound was prepared by conventional techniques and used to determine optical purity utilizing both a YMC-AKO3S-5300A, 25 cm, 4.6 mm OD chiral HPLC column (YMC Corporation) and a Pirkle convalent D-napthylalanine chiral column (Regis).

EXAMPLE 2

Di-p-toluoyl(L)-tartaric acid salt of cis α,α-3-amino-4-[2-(2-furyl)vinyl]-1-methoxycarbonyl-methyl-azetidin-2-one The title compound was provided by following the general procedure of Example 1, while substituting di-p-toluoyl-(L)-tartaric acid for di-p-toluoyl-(D)-tartaric acid.

Yield=75 mg; optical rotation= +40.9° at a concentration of 5.8 mg/ml at 25° C.

We claim:

1. The di-p-toluoyl-(D)-tartaric acid salt of cis ββ-3-amino-4-[2-(furyl)vinyl-1-yl]-methoxycarbonylmethyl-azetidin-2-one.

2. The di-p-toluoyl(L)-tartaric acid salt of cis αα-3-amino-4-(furyl)vinyl-1-yl]-methoxycarbonylmethyl-azetidin-2-one.

* * * * *